United States Patent [19]

Schoenthal et al.

[11] Patent Number: 4,730,072

[45] Date of Patent: Mar. 8, 1988

[54] PROCESS FOR PREPARING ALUMINOXANES

[75] Inventors: Galeon W. Schoenthal, Houston; Lynn H. Slaugh, Cypress, both of Tex.

[73] Assignee: Shell Oil Company, Houston, Tex.

[21] Appl. No.: 896,701

[22] Filed: Aug. 15, 1986

[51] Int. Cl.$^4$ ............................................... C07F 5/06
[52] U.S. Cl. ..................................... 556/179; 556/175; 556/187
[58] Field of Search ........................ 556/179, 175, 187

[56] References Cited

U.S. PATENT DOCUMENTS

| | | | |
|---|---|---|---|
| 3,300,458 | 1/1967 | Manyik et al. | 526/169 |
| 3,954,958 | 5/1976 | Matsui et al. | 556/179 X |
| 4,055,634 | 10/1977 | Brenner et al. | 556/179 X |
| 4,060,535 | 11/1977 | Cinco | 260/414 |
| 4,544,762 | 10/1985 | Kaminsky et al. | 556/179 |

*Primary Examiner*—Paul F. Shaver

[57] ABSTRACT

This invention relates to a process for preparing aluminoxines from trialkyl aluminum compounds and an water dispersion produced using a high speed, high shear-inducing impeller.

7 Claims, No Drawings

PROCESS FOR PREPARING ALUMINOXANES

FIELD OF THE INVENTION

This invention relates to a process for preparing aluminoxanes (also referred to as alumoxanes) which are useful in combination with transition metal compounds to prepare polymerization catalysts.

BACKGROUND OF THE INVENTION

Aluminoxanes find use as components in polymerization and oligomerization catalysts. Aluminoxanes have been prepared by reacting a hydrocarbon solution containing trialkyl aluminum with hydrated crystalline salts such as $CuSO_4.5H_2O$ ("Mechanism of Stereochemical Control in Propylene Polymerization with Soluble Group 4B Metallocene/Methylalumoxane Catalysts, *J. Am. Chem. Soc.*, 1984, 106, 6355–6364) and $Al_2SO_4.9-H_2O$ ("Zirconium Catalysts Polymerize Olefins Faster," Chem. & Eng. News, July 4, 1983, 29–30 and U.S. Pat. No. 4,544,762, issued Oct. 1, 1985). This technique requires guarding against the possibility of contaminating the aluminoxanes with small amounts of the crystalline salts which can act as poisons when the aluminoxanes are used in polymerization catalysts. In U.S. Pat. No. 3,300,458, issued Jan. 24, 1967 a method is disclosed for preparing aluminoxanes which consists of contacting trialkyl aluminum dissolved in a hydrocarbon solvent with a second hydrocarbon stream which has been saturated with water by contacting the solvent with water in a solvent saturator. In this technique, however, since the amount of water present in the hydrocarbon is small, being limited by the solubility of water in the solvent, relatively large amounts of solvent are required to prepare the aluminoxanes. Manyik et al in "A Soluble Chromium-based Catalyst for Ethylene Trimerization of Polymerization", *Journal of Catalysis*, 47, 197–209, (1977) also discloses the use of water wetted solvent and further discloses the use of the direct addition of water to a dilute solution of trialkyl aluminum. However, the water addition must be done very slowly in order to prepare the aluminoxane rather than aluminum hydroxide. One method for avoiding the problems that result from the use of water-wetted solvents and direct addition of water is to use the sonification procedure disclosed in co-pending application Ser. No. 896,689, filed 8/15/86. Another method is to use the process of the instant invention whereby water is dispersed in an organic solvent utilizing high speed stirring.

SUMMARY OF THE INVENTION

This invention relates to a process for preparing aluminoxanes which comprises mixing a first solution of a trialkyl aluminum compound in a liquid, dry, inert hydrocarbon solvent with a second solution of a liquid, inert, hydrocarbon solvent having water dispersed therein by means of high speed stirring. The use of the solution containing water dispersed by using a high speed, high shear-inducing impeller permits the use of minimal amounts of solvent and allows for a relatively rapid reaction rate to be used over a broad range of temperatures.

DETAILED DESCRIPTION OF THE INVENTION

The aluminoxanes (or alumoxanes) are well-known in the art and are polymeric aluminum compounds which can be represented by the general formula $(R-Al-O)_n$ which is a cyclic compound and $R(R-Al-O)_n AlR_2$, which is a linear compound. In the general formula, R is a $C_1-C_5$ alkyl group such as, for example, methyl, ethyl, propyl, butyl and pentyl and n is an integer from 1 to about 20. Generally, in the preparation of aluminoxanes from trialkyl aluminum and water, a mixture of the linear and cyclic compounds are obtained.

The aluminoxanes are prepared according to the invention by reacting a $C_1$ to $C_5$ trialkyl aluminum compound ($R_3Al$) in a suitable solvent with water which has been dispersed in a suitable solvent by means of high speed stirring. Illustrative examples of suitable trialkyl aluminum compounds are trimethyl aluminum, triethyl aluminum, tri-isopropyl aluminum, tri-n-propyl aluminum, tri-isobutyl aluminum, tri-n-pentyl aluminum, etc.

The inert solvents that can be used to dissolve the trialkyl aluminum or disperse the water are well known and include the saturated aliphatic compounds such as butane, pentane, hexane, heptane, octane, isoctane, the purified kersenes, etc.; the cycloaliphatics such as cyclobutane, cyclopentane, cyclohexane, cycloheptane, methylcyclopentane, dimethylcyclopentane, etc.; alkenes and cycloalkenes such as butene, hexene, cyclohexene, octene, etc., and the aromatic solvents such as benzene, toluene, xylene, etc.; and the like. The major requirements in the selection of a solvent are that it be liquid at the reaction temperature, that it does not react with the trialkyl aluminum compound or with water or interfere with any subsequent reaction wherein the aluminoxanes are used in polymerization catalysts. The solvents must be oxygen-free. Hydroxyl groups, ether groups, carboxyl groups, keto groups and the like adversely affect preparation of the aluminoxanes.

The aluminoxanes can be produced over a wide range of temperatures, from above the melting point of the solvent to up to the boiling point at the pressure used. Generally, temperatures below about 50° C. are used. Relatively low temperatures can be utilized with the appropriate solvent, say, −100° C. or lower. Pressures are not critical and will typically vary from atmospheric to about 500 psi.

There are numerous types of stirrers or impellers available commercially that can be used to disperse the water in the solvent. The high speed stirring of the instant invention involves the use of high speed, high shear-inducing impellers operating at greater than about 400 revolution per minute (rpm). The high speed stirring may be carried out in baffled vessels to enhance shear and water dispersion. The amount of water to be dispersed in the organic solvent ranges from just above the limits of solubility of water in the solvent to less than about 5% by weight. A preferred process of the instant invention is carried out by dispersing water in a suitable solvent using a high speed, high shear-inducing impeller, and, while maintaining the stirring, adding a solution of trialkyl aluminum to the water dispersion. Other variations of the process will occur to one skilled in the art. For example, after the water dispersion has been prepared, the high speed impeller can be shut off and the water dispersion slowly mixed with the trialkyl solution. The key here is to carry out the reaction prior to the breakup of the water dispersion. The dispersion, particularly for low concentrations of water, can be maintained for relatively long periods of time by cooling the dispersion. Satisfactory results have been obtained by cooling the dispersion to dry ice (−78.5° C.)

temperatures. The above reaction should be carried out in an inert, e.g., nitrogen or argon atmosphere.

After reaction, the solvent can be stripped and the aluminoxane isolated as a stable white powder. Preferably, however, the aluminoxane is left dissolved in the solvent, which can then be reacted with suitable transition metal compounds to form polymerization catalysts.

In general, the mole ratio of alkyl aluminum to water will be about 1:1 although variations of this ratio can occur without adversely affecting the aluminoxane product, i.e., the Al/water ratio can vary between about 0.66:1 to about 2:1, preferably about 0.75:1 to about 1.25:1.

The invention will be further described by the following examples which are provided for illustration and are not to be construed as limiting the invention.

EXAMPLE 1

The following represents a typical preparation of an aluminoxane at ambient conditions by the process of the instant invention.

The preparation was carried out in a 3-neck 100 ml Morton flask equipped with a high speed stirrer, a nitrogen inlet having a rubber septum for introduction of the aluminum trialkyl from a hypodermic syringe and a gas outlet. 30 Milliliters of toluene were added to the flask and 4 millimoles of water was added from a syringe while stirring at 1500 rpm. After 2 minutes of stirring and while maintaining the stirring, 4 millimoles (mmoles) of 25% wt trimethyl aluminum in toluene was injected with a syringe. Stirring was continued for about 2 minutes.

EXAMPLE 2

The above procedure was repeated at 50° C.

Embodiment Illustrating Use of Aluminoxanes in Catalyst Preparation

Part A

Oligomerization catalysts according to the teachings of co-pending application Ser. No. 896,700, filed Aug. 15, 1980, now U.S. Pat. No. 4,658,078 issued Apr. 14, 1987, were prepared and tested.

To the aluminoxane solutions of Examples 1-2, 0.5 mmole of bis(cyclopentadienyl)zirconium dichloride were added with stirring to prepare the catalysts. To examples 1 and 2 were added 50 ml of 1-hexene. The resultant mixtures were maintained at 40° C. for 2 hours before removing samples for gas chromatographic analysis. Conversions of 1-hexene to oligomers are given in the table below.

| Example | % Conversion of 1-Hexene |
|---|---|
| 1 | 80.8 |
| 2 | 3.7 |

Part B

Example 1 was repeated with the exception that differing amounts of water was used. To the thus prepared aluminoxane solutions were added 0.5 mmole of bis(cyclopentadienyl)-zirconium dichloride with stirring to prepare the catalysts. 400 Millimoles of 1-hexene were added with stirring to the thus prepared catalyst. The resultant mixtures were maintained at 40° C. for 30 minutes before removing samples for gas chromotographic analyses. The results are shown in the table below:

| Water added in Aluminoxane Preparation | % Conversion of 1-Hexene |
|---|---|
| 3 mmoles | 20.5 |
| 4.8 mmoles | 54.4 |
| 6 mmoles | 9.6 |

Part C

Example 1 was repeated with the exception that different stirring speeds were used. Catalysts were prepared and tested for 1-hexene oligomerization as per Part B above. The results are shown in the table below.

| Stirring Speed | % Conversion of 1-Hexene |
|---|---|
| 1500 | 36.2 |
| 750 | 30 |
| 500 | 21.2 |
| 250 | 11.9 |

We claim:

1. A process for preparing aluminoxanes which comprises mixing a first solution of a trialkyl aluminum compound in a liquid, dry, inert hydrocarbon solvent with a second solution of a liquid, inert, hydrocarbon solvent having water dispersed therein by using a high speed, high shear-inducing impeller wherein the trialkyl aluminum compound and the water react to produce an aluminoxane.

2. The process of claim 1 wherein the alkyl moiety of trialkyl aluminum compound is a $C_1$-$C_5$ alkyl group.

3. The process of claim 2 wherein the alkyl moiety is methyl or ethyl.

4. The process of claim 1 wherein the molar ratio of trialkylaluminum to water ranges from about 0.65:1 to about 2:1.

5. The process of claim 4 wherein the molar ratio ranges from about 0.75:1 to about 1.25.

6. The process of claim 5 wherein the molar ratio is about 1:1.

7. The process of claims 1, 2, 3, 4, 5 or 6 carried out at a temperature ranging from about −100° C. to about 50° C. and wherein the impeller is operated at a speed greater than about 400 revolutions per minute.

* * * * *